(12) United States Patent
Kamineni (10) Patent No.: US 7,574,844 B2
(45) Date of Patent: Aug. 18, 2009

(54) APPARATUS AND METHOD FOR INSTANTLY MANUFACTURING A BATCH OF CUSTOMIZED DOSAGE

(75) Inventor: Shobana Kamineni, Andhra Pradesh (IN)

(73) Assignee: M/S. Kei Vita Private Limited, Andhra Pradesh (IN)

( * ) Notice: Subject to any disclaimer, the term of this patent is extended or adjusted under 35 U.S.C. 154(b) by 761 days.

(21) Appl. No.: 11/143,280

(22) Filed: Jun. 2, 2005

(65) Prior Publication Data

US 2005/0210834 A1 Sep. 29, 2005

Related U.S. Application Data

(63) Continuation-in-part of application No. PCT/IN02/00229, filed on Dec. 4, 2002.

(51) Int. Cl.
*B65B 35/30* (2006.01)
*G05D 35/30* (2006.01)

(52) U.S. Cl. .............. 53/415; 53/900; 53/239; 700/239

(58) Field of Classification Search .......... 53/493, 53/415, 443, 147, 135.1, 239, 266.1, 900; 141/101–107; 700/233, 239, 240
See application file for complete search history.

(56) References Cited

U.S. PATENT DOCUMENTS

| | | | |
|---|---|---|---|
| 4,372,686 A | | 2/1983 | Herfeld |
| 4,870,799 A | * | 10/1989 | Bergerioux et al. ............. 53/55 |
| 4,964,262 A | * | 10/1990 | Moser et al. .................. 53/506 |
| 5,014,211 A | * | 5/1991 | Turner et al. ................ 700/239 |
| 5,040,699 A | * | 8/1991 | Gangemi ....................... 222/1 |
| 5,208,762 A | * | 5/1993 | Charhut et al. .............. 700/216 |
| 5,213,232 A | | 5/1993 | Kraft et al. |
| 5,329,459 A | * | 7/1994 | Kaufman et al. ............ 700/242 |
| 5,487,603 A | * | 1/1996 | Hoff et al. .................... 366/141 |
| 5,544,684 A | * | 8/1996 | Robinette, III ............... 141/83 |
| 5,622,692 A | * | 4/1997 | Rigg et al. .................... 424/63 |
| 5,629,863 A | * | 5/1997 | Palozzi et al. ............... 700/285 |
| 5,642,761 A | * | 7/1997 | Holbrook ..................... 141/104 |
| 5,690,283 A | * | 11/1997 | Sandolo ........................ 241/34 |
| 5,907,493 A | | 5/1999 | Boyer et al. |
| 6,260,332 B1 | * | 7/2001 | Takayanagi ................... 53/454 |
| 6,576,280 B2 | * | 6/2003 | Bebiak et al. ................ 426/232 |
| 6,959,284 B1 | * | 10/2005 | Howes ......................... 705/26 |
| 6,975,924 B2 | * | 12/2005 | Kircher et al. .............. 700/266 |
| 2002/0082745 A1 | * | 6/2002 | Wilmott et al. ............. 700/233 |
| 2003/0010791 A1 | | 1/2003 | Gentiluomo et al. |
| 2004/0172169 A1 | * | 9/2004 | Wright et al. ................ 700/265 |
| 2005/0087562 A1 | * | 4/2005 | Koide et al. .................. 222/252 |

FOREIGN PATENT DOCUMENTS

WO   WO 02/69897   *   2/2002

* cited by examiner

*Primary Examiner*—Paul R Durand
(74) *Attorney, Agent, or Firm*—William L. Botjer (57) ABSTRACT

An apparatus and a method for instantly manufacturing a batch of customized pharmaceutical dosages are provided. A batch of customized pharmaceutical dosages is manufactured as per the requirements of an individual, which may depend on age, gender, health, lifestyle, disease, habits, etc. The ingredients or components of the customized pharmaceutical dosages are selected as per the requirement of the individual. These ingredients or components are mixed/blended to form a homogenous mixture. The requisite quantities of the homogenous mixture, based on the individual's requirement, are then measured and converted to a desired final form, e.g., tablets, capsules or sachets. These tablets, capsules, etc., are then packaged and the packages are labeled.

11 Claims, 5 Drawing Sheets

APPARATUS AND METHOD FOR INSTANTLY MANUFACTURING A BATCH OF CUSTOMIZED DOSAGE

REFERENCE TO RELATED APPLICATIONS

This application is a CIP of PCT application number PCT/2002/IN000229, which designates the US and was filed Dec. 4, 2002 and whose priority is claimed.

BACKGROUND

The present invention relates to the field of manufacturing and dispensing pharmaceutical formulations. More specifically, it relates to the manufacturing and dispensing of pharmaceutical formulations instantly, as per the requirements of an individual.

The production of pharmaceutical formulations has been known in the art for a long time. Conventional methods provide processes for manufacturing pharmaceutical formulations in large quantities. The production of pharmaceutical formulations is carried out in a number of stages, using multiple machines. At each stage, separate machinery complete a part of the process, and the output of each stage is transferred to the next stage as input. Conventional systems do not provide a single-pass, instant process for manufacturing pharmaceutical formulations.

Large-scale manufacturing processes produce pharmaceutical formulations that can be used by any individual. These pharmaceutical formulations are given to everyone, regardless of individual requirements. Medical professionals have to depend on the choices offered by mass-produced formulations, rather than on prescriptions based on the requirement of individuals.

The large-scale manufacturing processes of pharmaceutical formulations take a long time. As a result, it is difficult to manufacture a pharmaceutical formulation instantly in the case of an emergency.

Further, it is not economical to produce small batches of pharmaceutical formulations, using large-scale manufacturing processes.

Additionally, the breakdown of any equipment disrupts the entire manufacturing process. Any disruption in the large-scale manufacturing process may result in the non-availability of some medicines in the market.

The factors mentioned herein have led to the development of systems for small-scale manufacturing of customized pharmaceutical formulations. Several systems for manufacturing and dispensing pharmaceutical formulations on a small-scale are known in the art. The systems for manufacturing and dispensing pharmaceutical formulations on a small scale are developed based on several systems used for other applications. One such system is described in U.S. Pat. No. 5,690,283.

U.S. Pat. No. 5,690,283, titled 'Coffee Blending and Flavoring Apparatus' discloses a coffee-blending and flavoring apparatus, which comprises a plurality of supply hoppers that contain a particular type of coffee bean. Each hopper has a scale discharge opening, to select the required quantity of coffee beans. The coffee beans are blended, and thereafter, a flavoring ingredient is added. The operations of the apparatus are CPU-controlled.

U.S. Pat. No. 4,372,686, titled 'Double-cone Rotating Mixer' discloses an apparatus for mixing materials. The disclosed rotating mixer comprises a double-cone mixing vessel that is carried by a horizontal mixer spindle. The mixing vessel consists of two identical half-vessels, which are clamped to a central spindle ring, in a manner that they can be released. The apparatus is designed to facilitate cleaning, to reduce the risk of contamination.

Several systems for manufacturing and dispensing pharmaceutical formulations have been developed that are based on the above-mentioned apparatus and similar apparatus. Some of the known pharmaceutical formulation systems are described below.

Glatt GmBH has disclosed the use of a semi-continuous system, 'Glatt Multicell GMC', for the granulation and drying of pharmaceutical products and foodstuff. The system finds application in the production of large and small batch sizes.

U.S. Pat. No. 5,907,493, titled 'Pharmaceutical Dispensing System', assigned to Innovation Associates, Inc., Johnson City, N.Y., discloses one such dispensing system. This system has a centralized workstation, monitoring an array of modules, each with a plurality of compartments loaded with pills, tablets or capsules. The system counts and dispenses a desired quantity of the medication, according to the given prescription.

Another system is described in U.S. Pat. No. 5,213,232, titled 'Rotating Apparatus for Dispensing Single Homogeneous Units', assigned to Owen Healthcare, Inc., Houston, Tex. The system comprises an apparatus for dispensing stored pharmaceutical medicines in the form of pills or capsules.

Yet another system is described in US patent publication number 2003/0010791 A1, titled 'Method and Apparatus for Dispensing a Customized Pharmaceutical Mixture', filed on Jul. 15, 2002. This patent application describes a method and apparatus for dispensing a customized pharmaceutical mixture. The quantities of the components that are needed to formulate a mixture are determined, based on health information particular to an individual.

However, each of these prior developments suffers from one or more of the following limitations.

Most prior art methods and systems manufacture the same dosages for all individuals, categorizing them as children or adults. These do not disclose any manufacturing process (of pharmaceuticals), wherein the dosage is customized as per the requirement of individuals, depending on their age, weight, sex, disease, lifestyle, etc. Moreover, prior art methods and systems do not disclose any instant pharmaceutical production system and the method or process of their manufacture.

SUMMARY

An object of the present invention is to provide a method and apparatus for instantly manufacturing a batch of customized pharmaceutical dosages in a single-pass process.

Another object of the present invention is to facilitate the availability of customized pharmaceutical dosages in a preferred form.

Yet another object of the present invention is to manufacture customized pharmaceutical dosages as per the requirement of an individual. These requirements may depend on age, sex, weight, lifestyle, disease, etc.

In accordance with one embodiment, the present invention provides a method and apparatus for instantly manufacturing a batch of customized pharmaceutical dosages, as per the specifications and requirements of an individual, such as individual-information pertaining to age, sex, weight, lifestyle, disease, habits, illness history, etc. The individual inputs the required information through a user interface. The system comprises a logic unit that generates customized dosage and process parameters based on these inputs. These customized dosage parameters include parameters such as ingredients, dosage and duration of dosage. The process parameters include parameters for preparing the pharmaceutical dosages according to customized dosage parameters.

Individual ingredients used to manufacture the customized dosage are stored in a bin assembly, from which required quantities of the selected ingredients are supplied to a dual blender unit. This operation is executed under the guidance of a microprocessor-based control unit. The dual blender assembly blends the selected ingredients to produce a homogenous mixture. The process of blending is controlled by the control unit, which controls the speed, angle and number of rotations. The homogenous mixture is then transferred to a conversion unit that prepares dosages in the desired final form, e.g., a tablet, capsule, sachet, or in liquid or gaseous form.

Once the dosages have been prepared in the final form, they are packaged and labeled. The label provides information pertaining to the ingredients in the dosages, customized for the individual. Other information, such as the individual's name, number of dosages required per day, etc., is provided on the label. Thereafter, the various modules of the system are cleaned to make sure that no residue of the ingredients, pharmaceutical formulation or dosages remains.

BRIEF DESCRIPTION OF THE DRAWINGS

The preferred embodiments of the invention will hereinafter be described in conjunction with the appended drawings, provided to illustrate and not to limit the invention, wherein like designations denote like elements, and in which.

DESCRIPTION OF THE PREFERRED EMBODIMENTS

The present invention provides an apparatus and a process for instantly manufacturing a batch of customized pharmaceutical dosages. These pharmaceutical dosages are customized as per the specifications and requirements of an individual, which may depend upon age, weight, sex, disease, lifestyle, etc.

Figure 1:
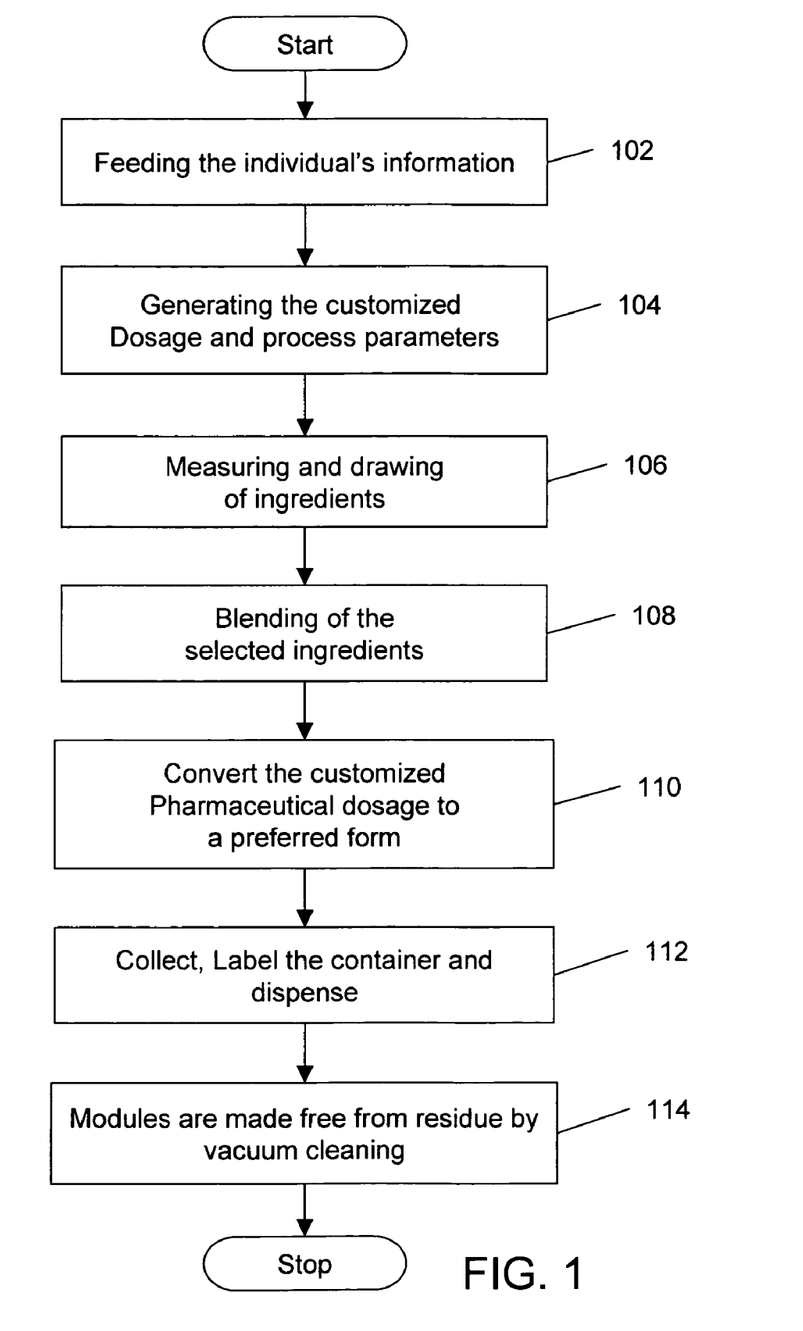
FIG. 1 is a flow chart that depicts a method for manufacturing a batch of customized pharmaceutical dosages, in accordance with an embodiment of the present invention.

FIG. 1 shows the steps involved in the process of manufacturing a batch of customized pharmaceuticals, in accordance with an embodiment of the present invention. At step 102, the individual provides information regarding his/her age, gender, ancestry, lifestyle, health, disease, etc., through a computer interface. In an embodiment of the present invention, the information supplied by the individual relates to his or her somatotype, lifestyle, health and illness. Somatotype information includes age, gender, ancestry, height, weight, etc. Lifestyle information includes nutrition, activity, stress and habits. Information pertaining to health includes medication, convalescence, fatigue, memory, well-being, etc.; information regarding illness includes history of present and past illness. The invention should not be considered limited only to the specified information. It will be apparent to one skilled in the art that any other information required to define and manufacture a customized dosage can be used.

Depending on the information received from the individual, the apparatus generates customized dosage and process parameters for manufacturing a batch of customized pharmaceutical dosages at step 104. Customized dosage parameters relate to defining the pharmaceutical formulation, ingredients, quantities of the ingredients, dosage, number of dosages for the entire treatment, etc. Process parameters include parameters for preparing the customized pharmaceutical dosages, such as measuring and drawing the specified quantities of the ingredients, parameters defining the ingredient-blending operation, measuring and drawing the specified quantity of pharmaceutical formulation for dosages, etc.

The ingredients or components required to manufacture the customized pharmaceutical formulation are selected at step 106, in accordance with the customized dosage parameters generated at step 104. The required amount of these selected ingredients are measured and drawn from a storage unit. At step 108, the selected ingredients are mixed/blended to produce a homogenous mixture.

After the mixing/blending operation is completed at step 108, customized pharmaceutical dosages are converted into a preferred form at step 110. These customized pharmaceutical dosages can be converted into solid, liquid or gaseous form, as per the requirement of the individual. At step 112, the customized pharmaceutical dosages are labeled and dispensed. Thereafter, the various modules of the process plant, used for performing steps 106-112, are cleaned to make them free from residue, which may otherwise contaminate subsequent dosages manufactured. Therefore, the various modules are vacuum-cleaned and readied for manufacturing next set of dosages.

As described at step 104 of the flowchart described in FIG. 1, customized dosage parameters and process parameters are defined according to information pertaining to an individual. An algorithm executed by a logic unit 150 (FIG. 2) in the apparatus defines these parameters. In an embodiment, logic unit 150 is a computer. This computer is connected to a database 152 (FIG. 2), which stores information regarding various diseases and their respective treatments and medications. The algorithm uses this information, and information about the individual, to define customized dosage parameters and process parameters.

Steps 106-114, as shown in FIG. 1, which are controlled by a microprocessor-based control unit 154 (FIG. 2), are based on the customized dosage parameters and process parameters generated by the logic unit. The microprocessor-based control unit is hereinafter referred to as a control unit. It is noted that logic unit 150 and control unit 154 may be embodied in a single computer. Control unit 154 obtains the defined parameters from logic unit 150 and controls the manufacturing process of the batch of customized dosages accordingly. The apparatus that manufactures the batch of customized dosages is discussed with reference to FIG. 2. The various elements of the process plant are controlled and guided by the control unit.

Figure 2:
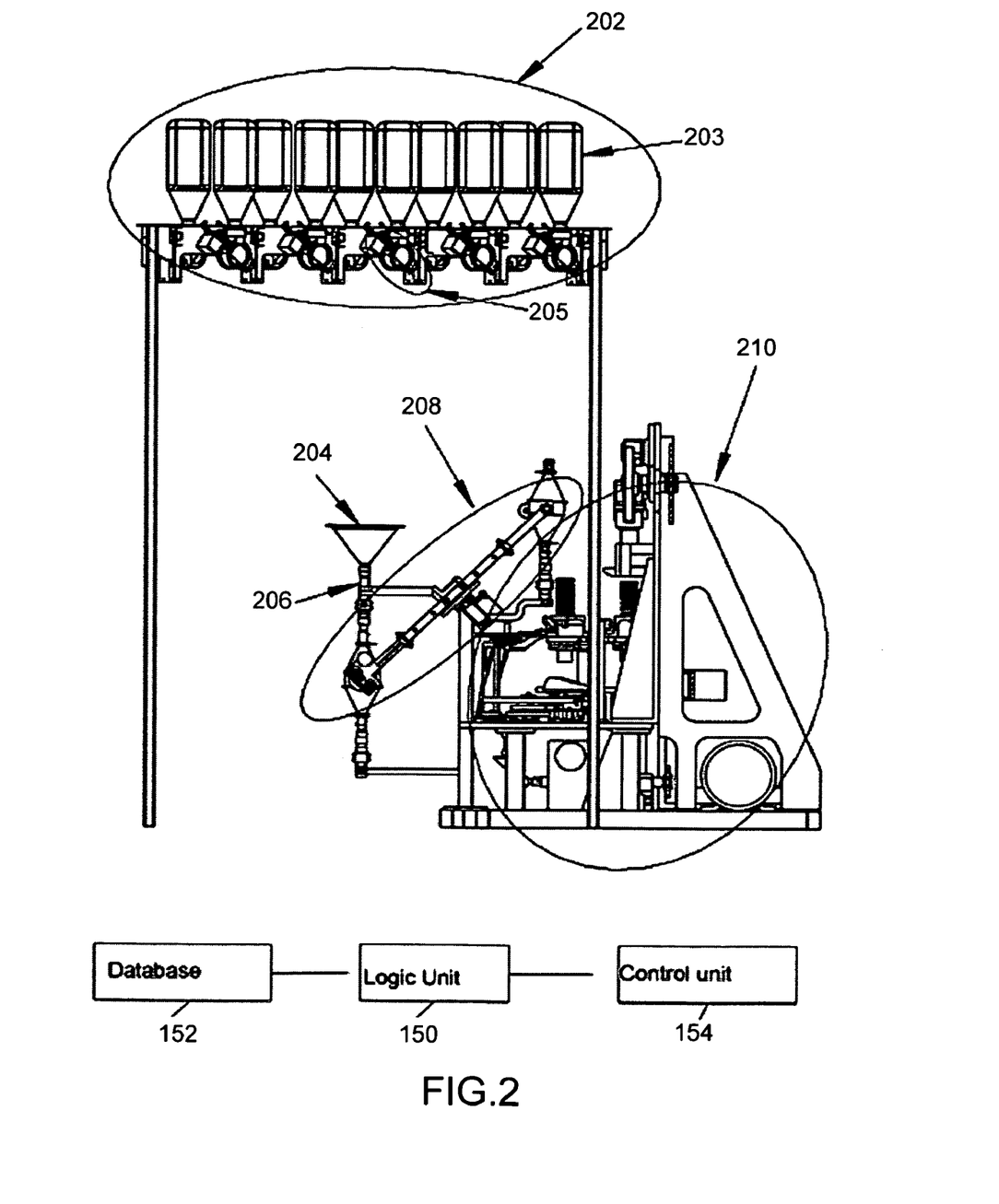
FIG. 2 shows an apparatus for manufacturing a batch of customized pharmaceutical dosages, in accordance with an embodiment of the present invention.

FIG. 2 shows an apparatus for manufacturing a batch of customized pharmaceutical dosages, in accordance with an embodiment of the present invention. The apparatus comprises a bin assembly 202, which is a multi-container assembly. Individual ingredients required to manufacture different pharmaceutical formulations are stored in separate containers 203 of bin assembly 202. Each container 203 in bin assembly 202 has a measure and draw mechanism 205 operated by control unit 154. Containers 203 are disposable, and one with a shortage of ingredients can be replaced with a filled container. Further, the number of containers 203 can be increased or decreased, depending on the requirements of the pharmaceutical to be dispensed. It will be evident to one skilled in the art that non-disposable containers can also be used in place of disposable containers, since they can be filled as and when required.

As already stated, depending upon the specifics and requirements of the individual, the logic unit generates customized dosage parameters such as ingredients, dosage, and the duration for which the dosages need to be taken. Based on this information, the control unit selects the containers and the quantity of the ingredient to be drawn from each container. The control unit facilitates the accurate measurement and drawing of the required ingredients from the various containers 203 in bin assembly 202 through the operation of measure and draw mechanism 205.

The required quantities of the selected ingredients are drawn from bin assembly 202. These ingredients are individually passed to a bin collector 204 through independent conveying tubes (not shown in FIG. 2 for the sake of clarity). The selected ingredients, collected in bin collector 204, are transferred via a common interface unit 206 to a dual blender unit 208, to prepare a homogenous mixture.

Common interface unit 206 is a conduit tube connecting bin collector 204 and dual blender unit 208. One end of common interface unit 206 is permanently attached to bin collector 204, and the other end has a controllable engagement mechanism that can be attached to/detached from dual blender unit 208. This controllable engagement mechanism links common interface unit 206 with dual blender unit 208 whenever bin collector 204 is in operation, to ensure free and spill-free delivery of the ingredients into dual blender unit 208. At the end of measuring and drawing operations, dual blender unit 208 will contain the required amount of each of the ingredients, as determined by the logic unit.

The ingredients are blended by the internal blades in dual blender unit 208, to produce a homogenous mixture in accordance with the process parameters. The homogeneous mixture thus produced is the customized pharmaceutical formulation, as determined by the logic unit. In the blending operation, different parameters such as the speed of rotation and number of cycles are controlled as per the process parameters generated by the logic unit. The operation of dual blender unit 208 is described in detail with reference to FIG. 3.

Once the homogenous mixture is prepared in dual blender unit 208, it is transferred to a conversion unit 210, which converts the customized pharmaceutical dosages to the preferred final form.

Figure 3:
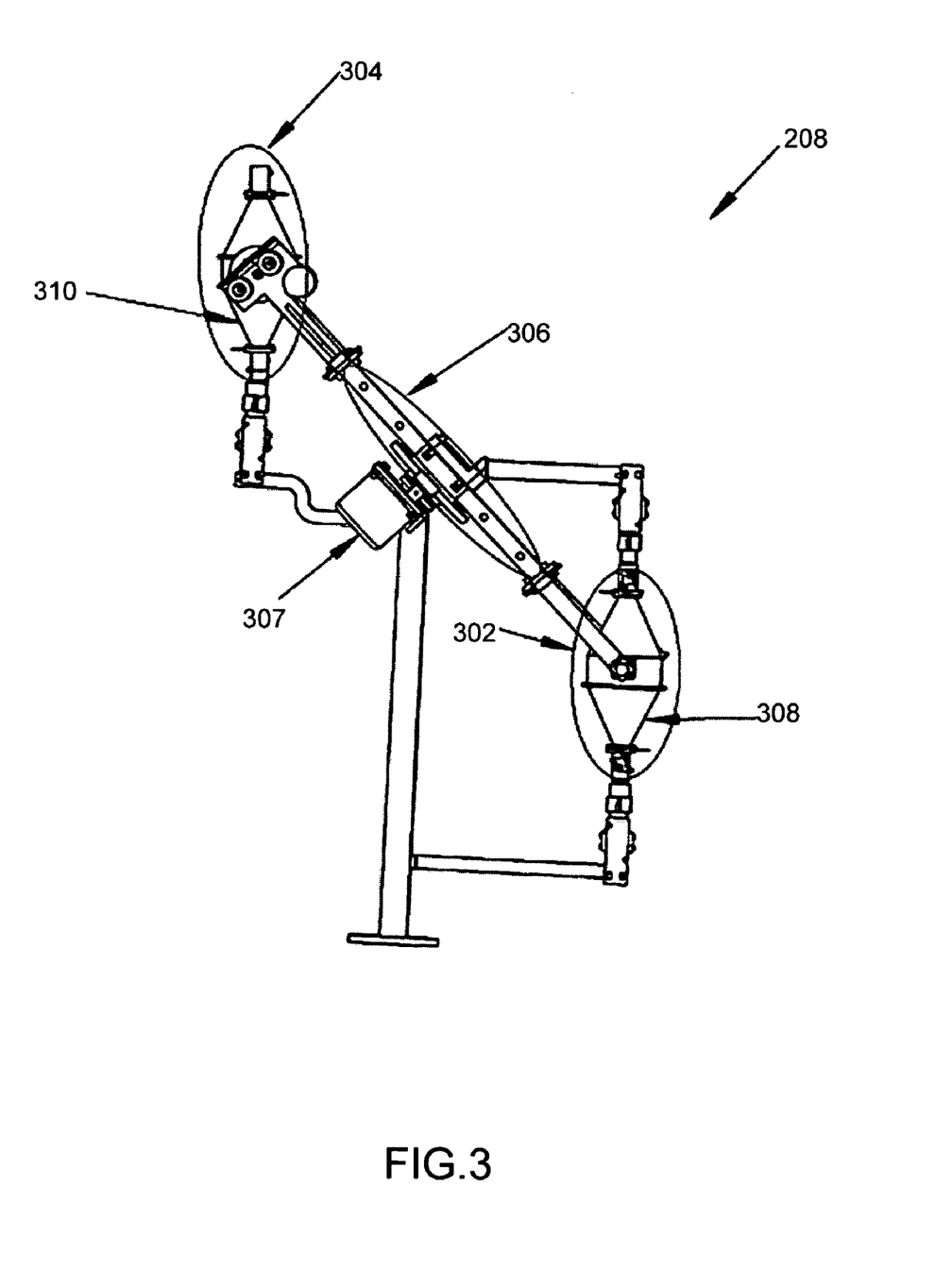
FIG. 3 shows a dual blender unit, in accordance with an embodiment of the present invention.

FIG. 3 shows dual blender unit 208, which comprises a first blender 302 and a second blender 304. First blender 302 and second blender 304 are fixed at the two ends of a rotatable angled support arm 306 operated by a motor 307 by the order of control unit 154. Both blenders can be used simultaneously. At a given time, one blender collects the ingredients and blends them to produce a homogenous mixture. Simultaneously, the second blender acts as a storage unit that feeds the homogenous mixture to conversion unit 210, and thereafter is cleaned. This enables continuous operation of the process plant. It will be evident to one skilled in the art that a single blender unit can also be used in place of a double blender unit. However, this would increase the process time for manufacturing the customized pharmaceutical dosage.

First blender 302 and second blender 304 operate in the following manner: The blender, at a lower position 308, receives the ingredients or components from bin collector 204. Then this blender goes through a blending cycle, preparing the homogenous mixture. Once the homogenous mixture is prepared, support arm 306 is rotated and the blender that was earlier at lower position 308, moves to a higher position 310. The other blender, which was at higher position 310, moves to lower position 308. The blender, now at a lower position 308, is cleaned and then goes through the procedure of collecting the ingredients from containers 203 and blending. Meanwhile, the blender that is now at a higher position 310 acts as a feeder for conversion unit 210. Once the blender at lower position 308 completes the blending operation and the blender at higher position 310 supplies the entire mixture to conversion unit 210, support arm 306 moves and exchanges the blenders' position.

From the operation of dual blender unit 208, it is apparent that the two blenders can be used simultaneously. While one blender draws the ingredients from bin collector 204 and blends the ingredients, the other blender supplies a homogenous mixture to conversion unit 210. The simultaneous operation of the two blenders enables the apparatus to function faster and in a more efficient manner.

Figures 4, 4A, 4B:
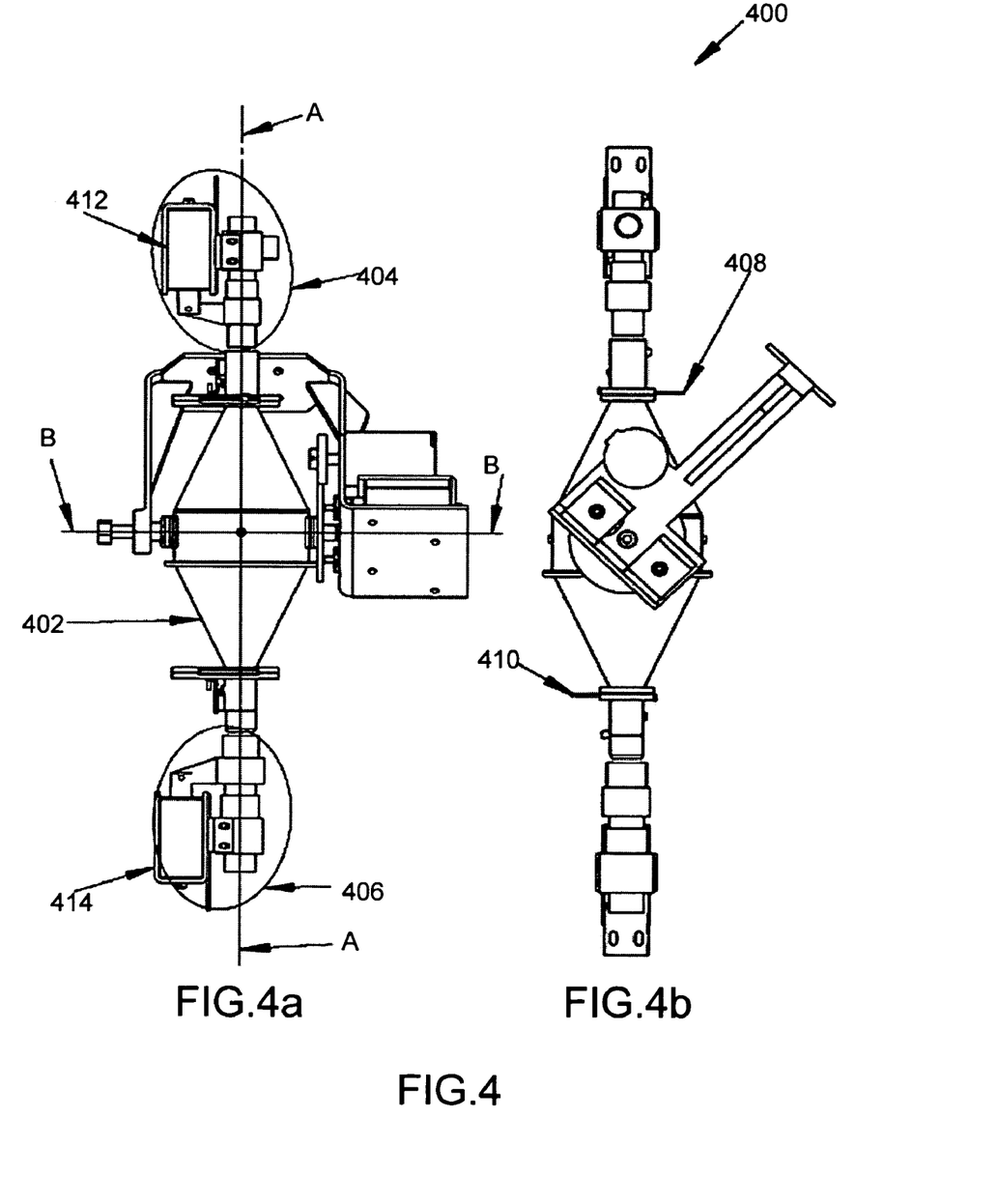
FIGS. 4a and 4b show a blender unit in two different views—a front view (4a) and a sectional view (4b) taken along line A-A of FIG. 4a, accordance with an embodiment of the present invention.

FIGS. 4a and 4b show a blender unit in two different views—a front view (4a) and a sectional view (4b) taken along line A-A of FIG. 4a. Blender 400 has a mixing mechanism for blending the ingredients. Control unit 154 controls various parameters such as the number of cycles and speed of rotation. Blending cycle programs are generated in advance by logic unit 150, depending on the customized pharmaceutical formulations to be manufactured.

Blender 400 mixes the ingredients or components by revolving a double conical container 402 about a symmetrical radial axis. Blender 400 contains a fixed internal changeable kneading blades that effectively and uniformly mix the ingredients as double conical container 402 revolves about the axis B-B as shown in FIG. 4a.

Blender 400 also has a controllable opening and closing mechanism (movable covers) at both the apex ends of double conical container 402. This mechanism allows the free entry of ingredients through a chute 404 while they are drawn into double conical container 402, and ensures that double conical container 402 is closed while blending is under operation. The apex conical ends are also adopted for easy engagement/disengagement with the adjacent units, common interface unit 206 and conversion unit 210.

Blender 400 contains inner blades (not shown in FIG. 4) for proper mixing or blending of the ingredients. A control unit 154 driven motor 406 controls the various cycles of rotation for proper blending or mixing. Motor 406 controls parameters such as the number of cycles and the rotation speed of blender 400. A homogenous mixture is obtained at the end of the blending process. Before the cycles of rotation start, the controllable opening and closing mechanism closes a top cover 408 and a bottom cover 410. The opening and closing of top cover 408 and bottom cover 410 is controlled by the control unit 154, operating motors 412 and 414.

The blending operation is controlled by the control unit through parameters such as the number of cycles, angles of rotation, and/or speed of rotation. These parameters are controlled to appropriately form the homogenous mixture. All these parameters govern the properties of the mixture, e.g., homogeneity, and required particle size and viscosity. All these parameters are crucial for producing pharmaceutical dosages, for example, non-uniformity in a mixture may result in a difference in the quantities of ingredients in different dosages (tables/capsules). If they differ, these dosages will contain pharmaceutical formulations that are different from the required customized formulation. This can adversely affect the course of treatment. Therefore, the parameters in the blending operation are accurately controlled by the control unit.

The homogenous mixture obtained from blender 400 is passed to conversion unit 210. Once the blending operation is completed, the controllable engagement mechanism at the bottom end of double conical container 402 engages with the receiving chute of conversion unit 210. After this engagement, the bottom end of double conical container 402 opens up, allowing the homogenously mixed ingredients to flow past it. Control unit 154 controls this opening mechanism.

The homogenous mixture is fed to conversion unit 210, which converts the received homogenous mixture to the final form, which can be a tablet, a capsule or a sachet, or any other form required.

Figure 5:
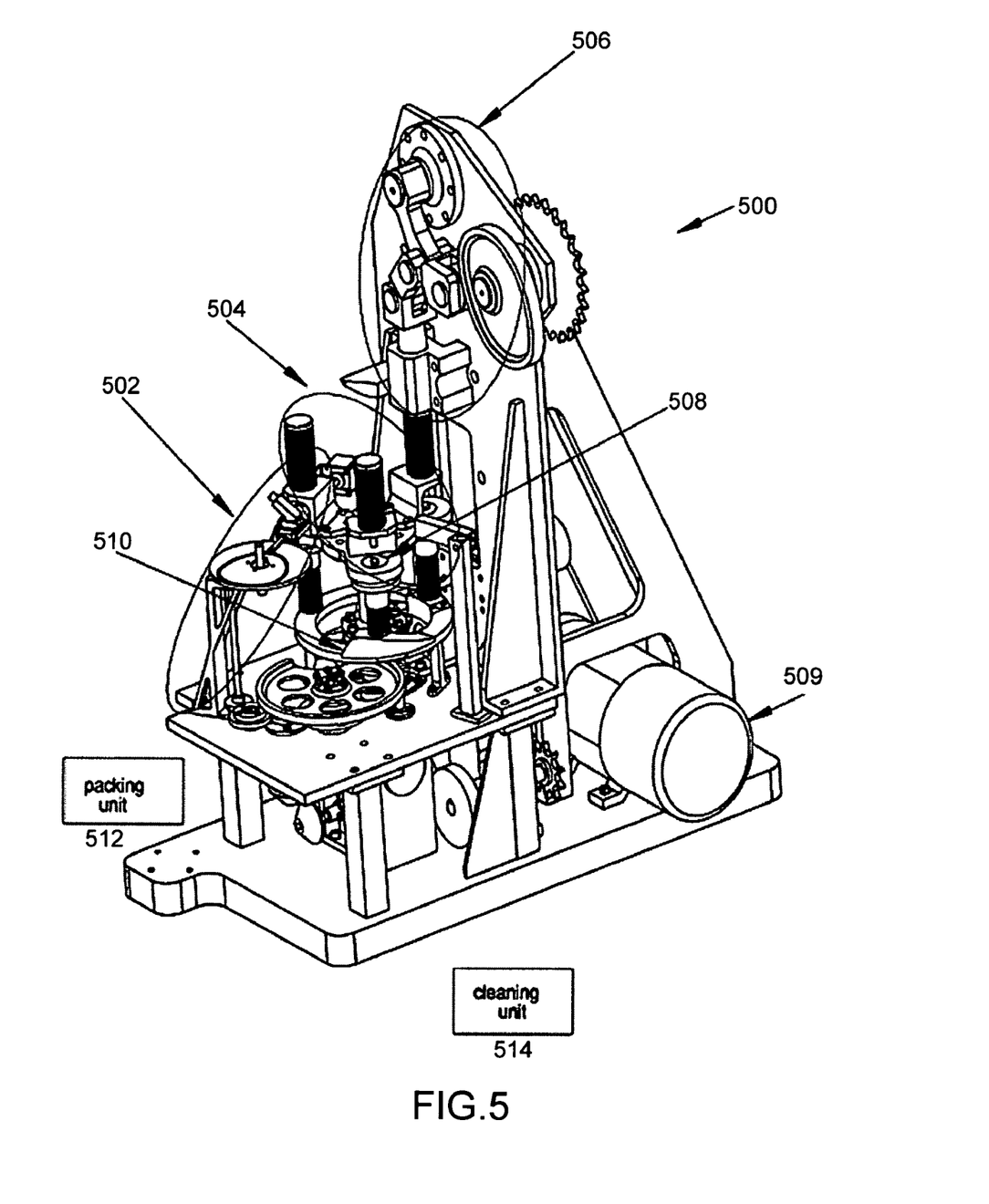
FIG. 5 shows a tablet conversion unit for converting a homogenous mixture to tablet form, in accordance with an embodiment of the present invention.

In one embodiment, conversion unit 210 is a tablet-conversion unit. FIG. 5 shows a tablet-conversion unit 500 for converting the homogenous mixture to a tablet form. Tablet conversion unit 210 converts the homogeneous mixture to a tablet form. It consists of a dosager assembly 502, a rotating table assembly 504, and a punch assembly 506. Dosager assembly 502 measures and draws the homogenous mixture from dual blender unit 208 through a connective chute. A die 508, in the shape of a tablet, is placed on table assembly 504. The conversion of the homogenous mixture in dosager assembly 502 takes place in three steps, which are governed by the rotation of table assembly 504. A motor 509 controls the rotation of table assembly 502. In the first step, table assembly 504 is rotated to a position, so that die 508 is under dosager assembly 502. Dosager assembly 502 measures the quantities of the homogenous mixture, depending upon the parameters generated by the control unit. The measured quantity of the homogenous mixture is drawn to a cavity in dosager assembly 502 and is then released from the cavity to die 508 on table assembly 504.

In an exemplary embodiment, the measurement of the homogeneous mixture in dosager assembly 502 is based on volumetric measurement. Volumetric measuring is based on the principle of a rectangular piston and a rectangular box, where the position of the piston determines the volume to be measured. The positioning of the piston is pre-calibrated to achieve the required volumetric space. This pre-calibration is carried out by experimental methods to ensure the correct dosage. It should not be considered that the invention is limited to volumetric measurement-based dosager assembly 502. It should be apparent to one skilled in the art that other measurement units, such as a weight measurement unit and the like, can also be used.

In the second step, table assembly 504 is rotated to a new position, so that die 508 on table assembly 504 is below punch assembly 506. Punch assembly 506 compresses the homogenous mixture in die 508 on table assembly 504 into a tablet.

In the third step, table assembly 504 is rotated to an ejection assembly 510. The tablet is ejected into a container by ejection assembly 510.

In another embodiment, conversion unit 210 is a capsule conversion unit, which converts the homogenous mixture to a capsule form. In addition to a dosager assembly and an ejection module, the capsule conversion unit consists of modules for opening the caps of empty capsules, for filling the homogenous mixture into the capsules, and for sealing the caps of the capsules. The filled capsules go into a container.

In yet another embodiment, conversion unit 210 is a sachet-filling unit that fills the homogenous mixture into sachets. This sachet-filling unit consists of a dosager assembly, an ejection module, and modules for filling and sealing the sachets.

After the customized dosages are obtained from conversion unit 210, they are passed to a packaging and labeling unit (shown as 512 in FIG. 5). The packaging and labeling unit 512 packages the dosages in appropriate containers and labels them. A printing attachment in packaging and labeling unit 512 prints the batch details on the pre-labeled containers. The labels contain details such as the date, the name of the patient, the composition, the dosage per day, the duration of the treatment, and other information. This information is obtained from the logic unit. It should be evident that these details will vary from one execution cycle of the process to another.

Once the process of manufacturing customized pharmaceutical dosages is over, material-handling units such as chutes, blenders, dosage-feeding mechanisms and conversion units are cleaned automatically. Any residues left behind can result in contamination of the pharmaceutical dosages in the next batches. This may adversely affect consumers' health.

A cleaning unit 514 carries out blowing and suction operations, and the entire residue is vacuumed into disposable bags. The various units of the apparatus are designed to facilitate cleaning operations. The design features that are taken into consideration include the geometry of the various units, the compatibility of the material used to design the various units, and the finish of the surface. The cleaning operation achieves cleaning to the level of 100 ppm. This operation ensures that all paths are free from residues.

The present invention offers the advantage of manufacturing a batch of customized pharmaceutical dosages in a single continuous process.

Another advantage of the present invention is that it facilitates the dispensing of a batch of customized pharmaceutical dosages in various forms. The customized pharmaceutical dosage can be dispensed in the form of tablets, capsules or sachets, etc.

Yet another advantage of the present invention is that it manufactures the customized pharmaceutical dosage instantly. Unlike other industrial manufacturing methods of manufacturing pharmaceutical dosages, with a large production time scale, the present invention provides an instantaneous method for preparing customized pharmaceutical dosages.

While the preferred embodiments of the invention have been illustrated and described, it will be clear that the invention is not limited to these embodiments only. Numerous modifications, changes, variations, substitutions and equivalents will be apparent to those skilled in the art, without departing from the spirit and scope of the invention, as described in the claims.

What is claimed is:

1. A method for instantly manufacturing a batch of dosages of a pharmaceutical formulation, the pharmaceutical formulation being customized as per the specifics and requirements of an individual, the method comprising the steps of:
   a. inputting the information about the specifics and requirements of the individual, the specifics and requirements of the individual including at least one of: somatotype, lifestyle, health, and illness information;
   b. generating process parameters and customized dosage parameters based on the inputted information relating to the specifics and requirements of the individual, the customized dosage parameters including parameters related to ingredients, dosage and duration, the process parameters including parameters related to measuring and drawing specified quantities of ingredients, ingredient-blending operation, measuring and drawing specified quantity of pharmaceutical formulation for the dosages;
c. selecting the ingredients based on the generated customized dosage parameters;
d. measuring and drawing the selected ingredients based on the generated process parameters;
e. blending the selected ingredients or components in a blender unit to obtain a homogeneous mixture, the blending comprising the steps of controlling at least one of: (a) speed of rotation, (b) angle of rotation, and (c) number of rotations of the blending unit, as per the generated process parameters; and
f. dispensing the batch of customized dosages.

2. The method of claim 1 further comprising the step of automatic cleaning of various units used to manufacture the customized dosages for obtaining a residue free manufacturing unit.

3. The method of claim 1 wherein the step of dispensing the batch of customized dosages comprises the steps of:
   a. measuring the homogeneous mixture for obtaining a single customized dosage;
   b. converting the measured homogeneous mixture into a final form;
   c. packaging the final form; and
   d. printing labels on the packaged final form, the labels representing the composition of the dosages.

4. The method of claim 3 wherein the final form of the customized dosage is tablet.

5. The method of claim 3 wherein the final form of the customized dosage is capsule.

6. The method of claim 3 wherein the final form of the customized dosage is sachet.

7. An apparatus for instantly manufacturing a batch of customized dosages of pharmaceutical formulations, the pharmaceutical formulations being customized as per the specifics and requirements of an individual, the system comprising:
   a. a logic unit, the logic unit generating customized dosage parameters and process parameters depending upon the specifics and requirements of the individual, the specifics and requirements of the individual including at least one of: somatotype, lifestyle, health, and illness information;
   b. a microprocessor based control unit, the control unit controlling the manufacturing process based on the generated customized dosage parameters and process parameters;
   c. a bin assembly, the bin assembly storing various individual ingredients that are required to manufacture the pharmaceutical formulations, in separate containers;
   d. a blender unit, the blender unit receiving the required quantities of the ingredients from the bin assembly as per the generated customized dosage parameters and process parameters, wherein the blender unit is a dual blender comprising:
      i. a first blender, the first blender having blades for blending the ingredients;
      ii. a second blender, the second blender having blades for blending the ingredients;
      iii. a movable support arm, the support arm connecting the first blender and the second blender, the support arm ensuring simultaneous functioning of the two blenders for a continuous operation, the support arm positioning the first blender and the second blender such that at a given time one blender receives and blends the ingredients, and the other blender connects to a conversion unit, and preparing a homogeneous mixture of the received ingredients by controlling at least one of: the speed of rotation, angle of rotation, and number of rotations of the blender unit as per the generated process parameters;
   e. the conversion unit converting the homogeneous mixture to a final form, the conversion unit being connected to the blender unit for receiving the homogenous mixture; and
   f. a packaging and labeling unit, the packaging and labeling unit packaging the final form of dosages and printing labels on the packaging.

8. The apparatus as recited in claim 7 wherein the conversion unit is a tablet conversion unit, the tablet conversion unit comprising:
   a. a dosager assembly, the dosager assembly measuring and drawing the required quantity of the homogeneous mixture for a dosage from the blender unit;
   b. a die for the tablet, the die receiving the homogenous mixture from the dosager assembly;
   c. a punch assembly, the punch assembly punching the homogeneous mixture in the die of the table assembly to produce a tablet; and
   d. a table assembly, the die being placed on the table assembly, the table assembly positioning the die for the dosager assembly operation and the punch assembly operation.

9. The apparatus as recited in claim 7 wherein the conversion unit is a capsule conversion unit, the capsule conversion unit filling the customized dosages into capsules.

10. The apparatus as recited in claim 7 wherein the conversion unit is a sachet conversion unit, the sachet conversion unit filling the customized dosages into sachets.

11. The apparatus as recited in claim 7 further comprising a cleaning unit for cleaning the dual blender unit, the conversion unit and all paths connecting various units of the system, the cleaning unit comprising:
   a. air blower means for blowing air to remove the residues left in the dual blender unit, the conversion unit and the paths connecting the various units; and
   b. a vacuum pump for suction of residue and transferring it into disposable bags.

\* \* \* \* \*